United States Patent [19]

Rosenfeld

[11] Patent Number: 5,450,855
[45] Date of Patent: Sep. 19, 1995

[54] METHOD AND SYSTEM FOR MODIFICATION OF CONDITION WITH NEURAL BIOFEEDBACK USING LEFT-RIGHT BRAIN WAVE ASYMMETRY

[76] Inventor: J. Peter Rosenfeld, 975 Vernon Ave., Winnetka, Ill. 60093

[21] Appl. No.: 185,434

[22] Filed: Jan. 24, 1994

Related U.S. Application Data

[63] Continuation-in-part of Ser. No. 882,434, May 13, 1992, Pat. No. 5,280,793.

[51] Int. Cl.⁶ .......................................... A61B 5/0482
[52] U.S. Cl. ..................................................... 128/732
[58] Field of Search ............................... 128/731, 732; 364/413.02, 413.05

[56] References Cited

U.S. PATENT DOCUMENTS

| | | | |
|---|---|---|---|
| 4,031,883 | 6/1977 | Fehmi et al. | 128/2.1 |
| 4,776,345 | 10/1988 | Cohen et al. | 128/731 |
| 4,928,704 | 5/1990 | Hardt | 128/732 |
| 4,955,388 | 9/1990 | Silberstein | 128/731 |
| 4,987,903 | 1/1991 | Keppel et al. | 128/732 |
| 5,036,858 | 8/1991 | Carter et al. | 128/732 |
| 5,269,315 | 12/1993 | Leuchter et al. | 128/731 |
| 5,299,118 | 3/1994 | Martens et al. | 128/731 |

OTHER PUBLICATIONS

Walters, Dale; Clinical Alpha-Theta Brainwave Training For Alcohol and Drug Addiction: 3-Day Workshop For Health and Mental Health Professionals. The Menninger Clinic, 1992.
Ochs, Len; EEG Addictions and PTSD. Center for Effective Living, 1992.
Mann, C. A.; Lubar, J. F.; Zimmerman, A. W.; Miller, C. A.; Muenchen, R. A.; Quantitative Analysis, etc. *Pediatric Neurology*, in press, 1992.
Schwartz, G. E.; Davidson, R. J.; Pugash, E.; Voluntary Control of Patterns of EEG Parietal Asymmetry: Cognitive Concomitants. *Psychophysiology*, 13, (1976), 498-504.
Peper, E.; Localized EEG Alpha Feedback Training: A Possible Technique For Mapping Subjective Conscious, and Behavioral Experiences. *Kybernetik*, 11, (1972), 166-169.
Tansey, M. A.; Righting the Rhythms of Reason: EEG Biofeedback Training as a Therapeutic Modality in a Clinical Office Setting. *Medical Psychotherapy*, 3, (1990), 57-68.
Peper, E.; Comment on Feedback Training of Parietal-Occipital Alpha Asymmetry in Normal Human Subjects. *Kybernetik*, 9, (1971), 156-158.
Peniston, E. G.; Kulkosky, P. J.; Alpha-Theta Brainwave Neuro-Feedback for Vietnam Veterans with Combat-Related Post-Traumatic Stress Disorder. *Medical Psychotherapy*, 4, (1991), 1-14.
Peniston, E. G.; Kulkosky, P. J.; Alcoholic Personality and Alpha-Theta Brainwave Training. *Medical Psychotherapy*, 4, (1990), 37-55.
Rickman, M. D.; Davidson, R. J.; Frontal EEG Asymmetry in Parents of Behaviorally Inhibited and Uninhibited Children. *Psychophysiology*, 28, (1991), p. S46 (Supplement).

(List continued on next page.)

*Primary Examiner*—George Manuel
*Attorney, Agent, or Firm*—Willian Brinks Hofer Gilson & Lione

[57] ABSTRACT

A method and system for treating a patient having a pathological condition characterized by asymmetry between brain waves measured from two locations of the scalp. The method comprises the steps of attaching a first electrode to a first scalp location of the patient and a second electrode to a second scalp location of the patient. Then, brain waves of the patient are recorded from the electrodes. These brain waves are used for the purpose of biofeedback. Specifically, the brain wave asymmetry is presented to the patient and the patient is rewarded for changing the asymmetry.

21 Claims, 1 Drawing Sheet

OTHER PUBLICATIONS

Tomarken, A. J.; Davidson, R. J.; Wheeler, R. E.; Resting Frontal Brain Asymmetry Discriminates Individual Differences in Repressive-Defensiveness. *Psychophysiology*, 28, (1991), p. S57 (Supplement).

Allen, J. J.; Iacono, W. G.; Depeu, R. A; Regional EEG Asymmetries in Bipolar Seasonal Affective Disorder and After Phototherapy. *Psychophysiology*, 28, (1991), p. S9.

Wells, G. B.; Moore, W. H., Jr.; EEG Alpha Asymmetries in Stutterers and Non-Stutterers: Effects of Linguistic Variables on Hemispheric Processing and Fluency. *Neuropsychologia*, 28, (1990), 1295-1305.

Matousek, M.; EEG Patterns in Various Subgroups of Endogenous Depression. *International Journal of Psychophysiology*, 10, (1991), 239-243.

Davidson, R. J.; Schaffer, C. E.; Saron, C.; Effects of Lateralized Presentations of Faces on Self-Reports of Emotion and EEG Asymmetry in Depressed and Non-Depressed subjects. *Psychophysiology*, 22, (1985), 353-364.

Henriques, J. B.; Davidson, R. J.; Regional Brain Electrical Asymmetries Discriminate Between Previously Depressed and Healthy Control Subject. *Journal of Abnormal Psychology*, 99, (1990), 22-31. (b).

Henriques, J. B.; Davidson, R. J.; Left Frontal Hypoactivation in Depression. *Psychophysiology*, 27, (1990), p. S38 (Supplement).

Nowlis, D. P.; Kamiya, J.; The Control of Electroencephalograhic Alpha Rhythms Through Auditory Feedback and the Associated Mental Activity. In: *The Nature of Human Consciousness*, edited by Robert E. Ornstein, W. H. Freeman and Company, 1973, 387-396. Originally published in *Psychophysiology*, 6, (1970), 476-484.

METHOD AND SYSTEM FOR MODIFICATION OF CONDITION WITH NEURAL BIOFEEDBACK USING LEFT-RIGHT BRAIN WAVE ASYMMETRY

REFERENCE TO RELATED APPLICATION

This application is a continuation-in-part of application Ser. No. 07/882,434 filed May 13, 1992, now U.S. Pat. No. 5,280,793 the entire disclosure of which is incorporated herein by reference.

BACKGROUND OF THE INVENTION

The present invention relates to a method and system for the treatment and analysis of depression or other disorders, and in particular, the present invention relates to a method and system for the treatment of depression that utilizes bio-feedback training based upon degree of left-right brain wave symmetry.

Two areas of subject matter may be considered relevant background for the present invention: biofeedback, and in particular EEG biofeedback, and EEG correlates of depression.

"Biofeedback" is a technique of making available to a person a record of one or more of his/her physiological activities to which he/she ordinarily does not have direct conscious access. A biofeedback technique may consist of measuring and recording a selected physiological variable and somehow communicating to the person the variable being measured on a moment-to-moment basis. For example, most people cannot accurately state their systolic or diastolic blood pressures on demand because these values are not available to conscious perception. To use biofeedback to make a person aware of his blood pressure, a pressure transducer could be surgically installed in the person's blood vessel and its voltage readout used to drive a meter whose needle the person could directly and consciously observe with his/her eyes.

Biofeedback therapy has been used to treat a variety of illness conditions with the use of various physiological parameters: e.g., hand-temperature feedback has been used to treat Raynaud's syndrome; EMG feedback has been used to treat neuromuscular disorders (pain, stroke, spasm); rectal sphincter tension feedback has been used to treat fecal incontinence, and so on.

"EEG Biofeedback" refers to the use of a subject's EEG activity as the physiological system that is used for biofeedback. "EEG" stands for electroencephalogram. An EEG is a graph showing voltage as a function of time, as this voltage is recorded from brain which generates it. The EEG is an always ongoing a series of waveforms (usually varying in frequency from 0.01 to 100 Hz) recorded from an electrode sensor placed on or in brain, or more typically, on the scalp surface. This scalp sensor is known to measure ongoing, spontaneous bioelectric signals generated by underlying cerebral cortex. In principle, all cognitive and other mental activities occurring in cortex are associated with specific bioelectric cortical activities. There are a variety of attributes or properties by which an EEG can be characterized. Amplitude, frequency, and rhythmicity (synchronous or frequency-recurrent versus asynchronous) are the most typical. Every lead (sensor) one can attach to the scalp is able to sense the EEG at that locus. Thus, one can speak of relative amounts of some activity between any specified pair of loci.

EEG biofeedback is relatively old. Nowlis and Kamiya summarized their 1960's experiments more than 20 years ago (Nowlis, D. P. and Kamiya, J. The control of electroencephalographic alpha rhythms through auditory feedback and the associated mental activity. In: *The Nature of Human Consciousness*, edited by Robert E. Ornstein, W. H. Freeman and Company, 1973, 387–396. Originally published in *Psychophysiology*, 6 (1970) 476–484). In those days, the thrust of EEG biofeedback was to train subjects to produce more alpha activity in single, central scalp locations. The aim was to provide relaxation, good-feeling, and a sense of wellness. This literature has led to relaxation therapies which are presently used to reduce stress in tense persons. Despite its fairly widespread usage, simple alpha-biofeedback-based relaxation is not an established psychiatric/therapeutic approach.

There are a few other reports in which investigators used single site EEG biofeedback for therapeutic effects. In these studies, the EEG activity subjected to biofeedback is somewhat more complex than in the older alpha literature. These newer approaches require subjects to generate more EEG of a given frequency and less of another frequency, or to increase two different frequencies at the same time. Mann, Lubar, Zimmerman, Miller, and Muenchen (1992) are concerned with curing children with attention deficit disorder (Mann, C. A., Lubar, J. F., Zimmerman, A. W., Miller, C. A., and Muenchen, R. A. Quantitative analysis, etc. *Pediatric Neurology*, in press, 1992). They train patients to produce more beta activity (>13 Hz) and less theta (5–7 Hz), and have claimed great success. Peniston and Kulkosky (1991 and references) have reported that training persons to increase alpha and theta activity is good for a variety of ills, from alcoholism to post-traumatic stress disorder (Peniston, E. G., and Kulkosky, P. J. Alpha-theta brainwave neuro-feedback for vietnam veterans with combat-related post-traumatic stress disorder. *Medical Psychotherapy*, 4 (1991) 1–14). Tansey (1990) describes a therapeutic use for EEG biofeedback in which increased beta (14 Hz) at a single scalp site is used to allegedly improve cognitive function in learning disabled children (Tansey, M. A. Righting the rhythms of reason: EEG biofeedback training as a therapeutic modality in a clinical office setting. *Medical Psychotherapy*, 3 (1990), 57–68). There are a series of studies by Sterman and colleagues from the 1970's in which increased 12–14 Hz single site EEG biofeedback was used to treat epilepsy.

"EEG alpha asymmetry" refers to the relative amount of rhythmic (repeating) alpha (8–12 Hz) frequency in the left side of scalp relative to the right side. (Note an EEG lead requires at least two connections to complete the circuit: (i) the "active" site on scalp over the critical brain region generating the signal of interest, and (ii) a "reference" locus, a part of the patient which is neurologically "quiet," e.g., an earlobe or skin over the mastoid bone. Typically, a third electrode is connected between the subject at another "quiet" spot and system ground.)

There are a few published studies of EEG biofeedback where two-site symmetry was the training parameter used, however these were not therapeutically oriented. Peper (1971, 1972) did some early demonstration that indirect left versus right alpha biofeedback was possible to demonstrate, and that it might be used diagnostically to see what kind of psychological states go with the various, biofeedback-trained (a)symmetries (Peper, E. Comment on feedback training of parietal-occipital alpha asymmetry in normal human subjects.

Kybernetik, 9 (1971), 156–158. Peper, E. Localized EEG alpha feedback training: A possible technique for mapping subjective, conscious, and behavioral experiences. Kybernetik, 11 (1972), 166–169).

Schwartz, Davidson, and Pugash (1976) reported that left-right parietal (not frontal) alpha (a)symmetry biofeedback control could be learned by subjects (Schwartz, G. E., Davidson, R. J., and Pugash, E. Voluntary control of patterns of EEG parietal asymmetry: Cognitive concomitants. Psychophysiology, 13 (1976), 498–504). Schwartz et al. go on to report that more "emotional thinking" tended to accompany some of the training modalities. Their aims were, like Peper's, to see if symmetry and asymmetry biofeedback were possible, and also, to learn what the "cognitive" concomitants of trained (a)symmetry were.

Depression may be considered a pathological mental state associated with pathological EEG activity. "EEG correlates of depression" refer to recordable signs in the EEG which correlate with and thus may be symptomatic of depression. Pollock and Schneider (1990) reviewed the literature on the topic of EEG correlates of depression in awake subjects and Kupfer and Frank (1984—cited in Pollock & Schneider's references) did the same task for sleeping EEG samples (Pollock, V. E. and Schneider, L. S. Quantitative, waking EEG research on depression. Biol. Psychiatry, 27 (1990) 757–780; Kupfer, D. J. and Frank, E. The relationship of EEG sleep to vital depression. J. Affect Dis., 7 (1984) 249–263). The bulk of this work establishes that, despite some inconsistencies, depressed subjects show characteristic frequency attributes from single site sets of recordings.

More relevant to present concerns, however, are a series of reports from Davidson's lab which describe EEG regional asymmetries as highly reliable correlates of depression. Henriques and Davidson, (1990) have reported that, in comparison to normal individuals, depressed individuals have an abnormal electroencephalogram (EEG) pattern involving more left than right frontal alpha power and/or more right than left parietal or temporal alpha power (Henriques, J. B. and Davidson, R. J. Left frontal hypoactivation in depression. Psychophysiology, 27 (1990), p. S38 (Supplement). (a) Henriques, J. B. and Davidson, R. J. Regional brain electrical asymmetries discriminate between previously depressed and healthy control subject. Journal of Abnormal Psychology, 99 (1990) 22–31.(b). Davidson, R. J., Schaffer, C. E. and Saron, C. Effects of lateralized presentations of faces on self-reports of emotion and EEG asymmetry in depressed and non-depressed subjects. Psychophysiology, 22, (1985) 353–364). Matousek (1991) has provided recent confirmation (Matousek, M. EEG patterns in various subgroups of endogenous depression. International Journal of Psychophysiology, 10 (1991) 239–243). Others have shown EEG asymmetry correlates of other emotion-related conditions (e.g., Wells, B. G. and Moore, W. H., Jr. EEG alpha asymmetries in stutterers and non-stutterers: Effects of linguistic variables on hemispheric processing and fluency. Neuropsychology, 28 (1990) 1295–1305; Rickman, M. D. and Davidson, R. J. Frontal EEG asymmetry in parents of behaviorally inhibited and uninhibited children. Psychophysiology, 28 (1991), p. S46 (Supplement); Tomarken, A. J., Davidson, R. J., and Wheeler, R. E. Resting frontal brain asymmetry discriminates individual differences in repressive-defensiveness. Psychophysiology, 28 (1991) p. S57 (Supplement); Allen, J. J., Iacono, W. G., and Depue, R. A. Regional EEG asymmetries in bipolar seasonal affective disorder before and after phototherapy. Psychophysiology, 28, (1991) p. S9 (Supplement)).

Accordingly, it is an object of the present invention to provide a biofeedback method for the treatment of depression based upon the characteristic asymmetric brain wave pattern associated therewith.

It is a further object of the present invention to provide a method and system for the treatment of a pathological condition of a patient that is characterized by any brain wave asymmetry.

SUMMARY OF THE INVENTION

The present invention comprises a method and system for treating a patient having a disorder characterized by a pathological asymmetry between brain waves measured from two locations of the scalp. The method comprises the steps of attaching a first electrode to a first scalp location of the patient and a second electrode to a second scalp location of the patient. Conventional reference and/or ground electrode connections to the patient are also made. Then, brain waves of the patient are recorded from the (appropriately referenced) first and second electrodes. These brain waves are used for the purpose of biofeedback. Specifically, a perceivable index of the brain wave asymmetry is presented to the patient and the patient is rewarded for changing asymmetry.

In a first aspect of the present invention, the method is used for the treatment of depression. The present invention comprises recording (appropriately referenced) left-of-midline and right-of-midline frontal or parietal EEG and signaling subjects whenever the EEG symmetry (which randomly varies around a symmetry mean in all persons) takes a drift in a "healthy" direction, i.e., whenever there is a momentary decrease in left frontal and right parietal power, relative, respectively, to right frontal and left parietal power. "Alpha power" means more synchronously sinusoidal alpha activity (8–12 Hz) in the EEG than other activity, especially in this case desynchronized "beta" activity in the $>14$ Hz range. The low voltage Beta desynchronization is associated with cortical "arousal" or "activation" so that "less activation"="more alpha." Thus, depressed individuals have reduced left frontal activation/arousal =more left frontal alpha. "Alpha power" is a measure of alpha (8–12 Hz) activity sometimes obtained by calculating power by voltage integration using spectral analysis via (fast) Fourier Transforms. The alpha may be determined by any suitable means. For example, a narrow bandpass filter and computer system may be used which passes only alpha (8–12 Hz) and sums the area under the curve of passed, rectified waveform. Differences between left and right derivations are compared, and when they are "in the correct direction," a reinforcement signal is given. This signal can take any standard (existing) form: i.e., a visual display, meter needle, or acoustic output. It does not matter how the patient is signaled of his correct behavior, only that he is signalled. In other words, patients who are depressed produce a specific EEG symmetry pattern. Healthy (non-depressed) persons produce a different pattern. The invention provides for using biofeedback to train the "sick" person to help cure himself by producing the "healthy" EEG symmetry pattern.

BRIEF DESCRIPTION OF THE DRAWING

The Figure is a schematic representation of the connections between a patient's scalp and an EEG biofeedback apparatus for practicing a method according to a first embodiment of the present invention.

DETAILED DESCRIPTION OF THE PRESENTLY PREFERRED EMBODIMENTS

EEG Recording Method

Figure 1:
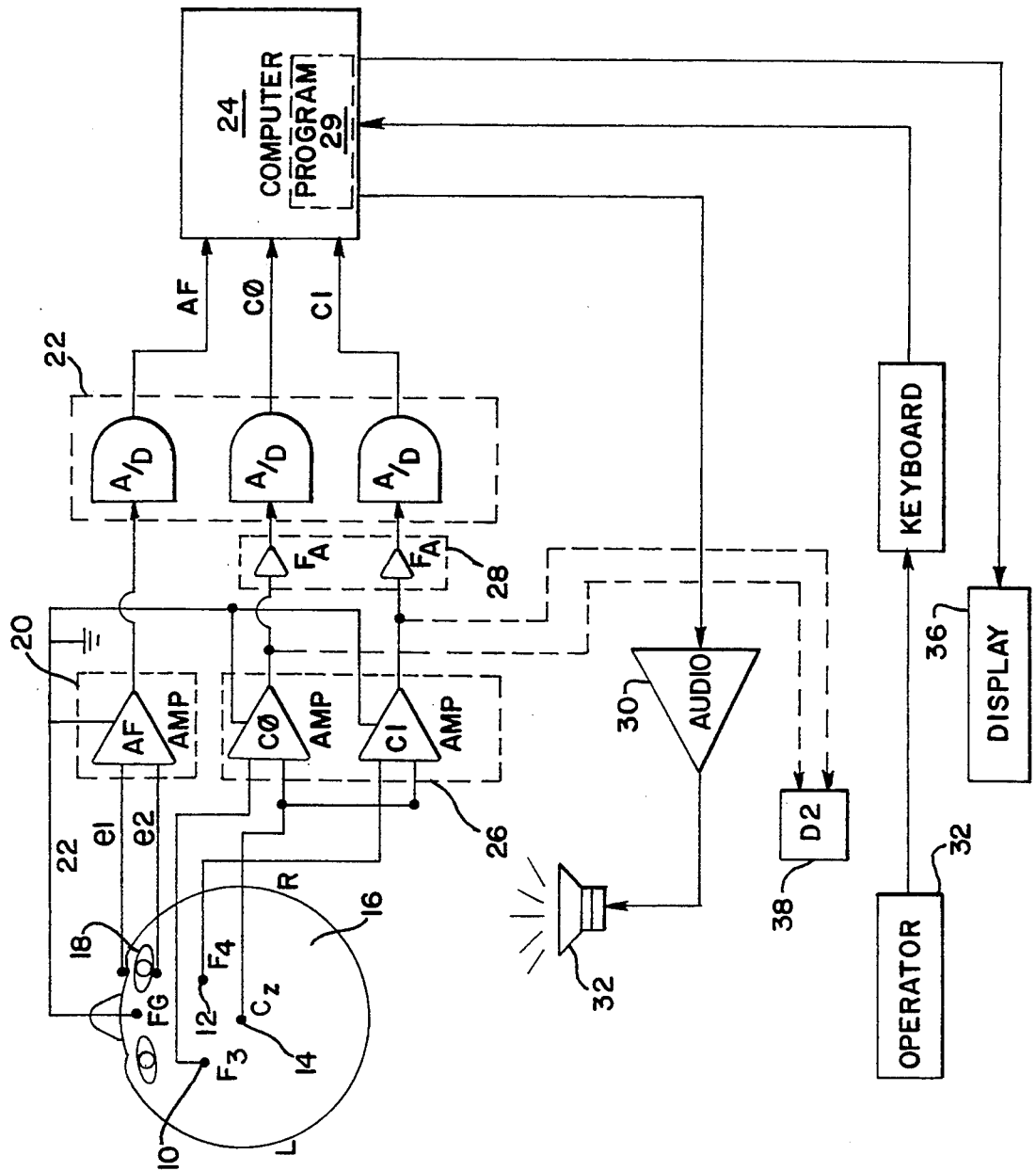

To voluntarily control with biofeedback (hereafter this process will be denoted as: to "condition" or "operantly condition") left-right alpha asymmetry (hereafter "ALAY"), one needs to select (minimally) one left-of-midline (hereafter "left") site, and one right-of-midline (hereafter "right") site. Davidson's group reported that the mid-frontal sites ($F_3$ and $F_4$ in the standard 10-20 system of Jasper, H. H., *Electroenceph. Clin. Neurophysiol.*, 1958, V. 10, 371-375) constitute the most reliable pair of left-right sites (both referenced to Cz) from which to record ALAY as a correlate of depression, (Henriques & Davidson, *Psychophys.*, 27, 1990, p. S. 38). However in some of their studies, ALAY from the posterior temporal ($T_5$ and $T_6$) and parietal ($P_3$ and $P_4$) electrodes also correlated reliably (Henriques & Davidson, *J. Abnormal Psych.*, 99, 1990, 22-31). In the case of frontal sites, the asymmetry is defined by more left (than right) alpha, whereas in the parietal and temporal sites, the depression-related asymmetry is defined by less left (than right) alpha.

There are thus several possible variants on the EEG biofeedback general procedure to be described herein. One could positively reinforce ("reward") subjects for (i): decreasing left frontal alpha, (ii): increasing right frontal alpha, (iii): both (i) and (ii), (iv): increasing left parietal alpha, (v): decreasing right parietal alpha, (vi): both (iv) and (v), (vii): both (iii) and (vi), (viii): increasing left temporal alpha, (ix) decreasing right temporal alpha, (x): both (viii) and (ix), (xi): all three of (iii) and (vi) and (x), and so forth, including various further combinations of the above reinforcement contingencies. The general idea of these embodiments—converting a pathological EEG pattern to a healthy one through operant (biofeedback) conditioning of ALAY—remains the same no matter which combination is used. Moreover, additional research may demonstrate that some combinations obtain better results with some patients and other combinations obtain better results with other patients. Since the $F_3$ and $F_4$ pair are regarded as the pair showing the most reliable ALAY correlate of depression, in the first embodiment described in detail as follows, only this pair is used, as in variant (iii) above. However after this, it will be briefly shown how one might combine (iii) and (vi) (i.e., into (vii)) in further embodiments.

Referring to the Figure, using conventional procedures (e.g., Binnie, Rowan, and Gutter, *A Manual of Electroencephalographic Technology*, Cambridge University Press, 1982), electrodes 10, 12, and 14 are attached to the scalp 16 of a patient at $F_3$, $F_4$ and Cz. Cz is used as the common reference for $F_3$ and $F_4$, the active sites, left and right respectively, in a standard recording configuration with the subject grounded at FG, the forehead center. (Other referencing montages may also be used). Additionally, electrodes e1, e2 are placed above and below either eye 18 for ocular artifact detection; these electrodes e1, e2, form a bipolar pair of leads. Thus, three channels of information are derived from the subject: the left, mid-frontal EEG ($F_3$) called channel zero (C$\emptyset$), the right, mid-frontal EEG ($F_4$) called channel 1 (C1) and the eye movement-ocular artifact channel (AF). The latter goes to a conventional biological amplifier 20. For example, a Grass Electronics P5J biological amplifier with gain=80,000 to 100,000 and filters set to pass signals from 3 to 100 Hz may be used. From the biological amplifier 20, the signals are conveyed to a commercially available analog-to-digital converter (A/D) 22 interfaced to a standard digital microcomputer 24 (e.g., Commodore C128, IBM AT, etc). C$\emptyset$ and C1 also go to a biological amplifiers 26 with gain=50,000 to 200,000 and filters set to pass signals from 0.3 to 30 Hz. Prior to passage to A/D converters, however, C$\emptyset$ and C1 are passed through commercially available narrow alpha bandpass filters ($F_A$) 28 which have a flat, 100% signal passage frequency response between 9 and 11 Hz, but which pass 50% of the signal at 8.5 and 11.5 Hz. At 7.5 and 12.5 Hz, <10% of the input EEG signal passes. The filtered C$\emptyset$ and C1 then pass to A/D 22 and computer 24.

The computer 24 runs a program 29, such as ALAY11, by J. P. Rosenfeld. The program 29 is written in BASIC which is then compiled with the "BASIC 128" compiler by Abacus Co., (Grand Rapids, Mich.). The program listing AYAY11 (included in Appendix 1) shows the source (uncompiled) code in Commodore BASIC 7.0. When compiled, this program becomes M-ALAY11. This program 29 serves to collect various types of baseline samples (in baseline sessions, the subject does not get "rewards" contingent on ALAY values) of ALAY and provides ALAY statistics for the session at its end, so that biofeedback criteria for future ALAY training can be generated, as described below.

After baseline session(s), the same program 29 may also used for ALAY training. The variable GL (see Line 65 of the program listing in Appendix 1) is given the actual ALAY training "CRITERION TO BEAT" and when GL is exceeded, a reward is given, as in Line 162. The "reward" may be a pleasant-sounding tone, as in the present embodiment. If, and only if, SA (the ALAY Score for the current sample) exceeds GL (the goal or criterion), is the "SOUND" given. This "SOUND" instruction, in the Commodore 128 computer 24, causes a low voltage sine wave to be output from the sound generating circuit of the computer 24 which then goes to a standard audio power amplifier ("Audio") 30 which amplifies it so that it can drive the loudspeaker 32 which the subject can hear.

Line 5 gives the compiler directive instructions. The "SETUP" section begins in Line 22 and inputs from the operator 33 the parameters for the present run of the program, e.g., Lines 65-95 (1) inputs the criterion for reward in a training session; (in a baseline session, any number is input and the audio (reinforcement) amplifier 30 may be turned off. It is also possible and preferable to give in baseline a randomly determined reward occurrence via Lines 55, 158-159, as explained further below; (2) determines if there will or will not be a display to the operator of the current sweep or trial, which is a sample of filtered EEG from the subject; (3) determines if there will or will not be a post-session printout; (displays and printouts can be avoided to save time); (4) determines how long the reward and artifact tones will last (variables RW and AD); (5) takes the subject's name and records whether the session is a baseline sample or a training session (Line 66); (6) determines how long the inter-trial interval will be (variable IT, Line 70); (7) determines how often the brain waves will be sampled (variable IS, Line 70; this is typically set=to 10 to yield a 200 Hz EEG sampling rate); (8) determines (Line 95) the number of brain wave samples (for each electrode) per sweep (variable RR, presently set to =100 or 200 to yield (5 msec×100=) 500 msec or (5 msec×200=) 1.0 sec sweeps, respectively. For an average alpha wave of 100 msec wavelength (10 Hz frequency), these recording epochs will yield (respectively) five complete alpha waves (RR=200); (9) determines (Line 90) the number of sweeps per session (variable=TR; the trials loop (line 100) thus runs from 1 to TR). The other operations of the set-up simply define some variable values including the operator display parameters.

The next section of the program 29 is the EEG sampling loop (Lines 102–127). Here, the left electrode is sampled ("L(SM)=PEEK (C2)"), then the right ("R(SM)=PEEK (CO)"). (Although "C2" is addressed, it is channel ∅ (left electrode) value which is returned. Likewise, peeking "CO" actually returns the value of the right EEG, Channel 1. This off-set addressing mode is necessitated by the peculiarity of the A/D converter used.) Line 112 samples the AF (artifact channel) and if there is an artifactual value ("ZE" or "FF", corresponding to 40 μV, peak-to-peak) in the eye channel, the artifact sound (Line 112), a buzz, may be presented, as described below, to tell the subject to hold still and/or stop blinking, but whether the subject is or is not signaled, the trial is restarted (Line 126: "GO TO 105").

These operations are repeated RR times (Line 105 "FOR SM=1 TO RR") until one-dimensional arrays of left EEG values, L(SM), and right EEG values, R(SM), with SM running from 1 to RR, are collected. These are then rectified and integrated (Lines 129–140, "RECT & MATH:) to yield approximations of total area (power) under the left and right alpha curves. This is done by accumulating all the L(SM) and R(SM) values for the trial into the sums SL and SR (Line 140).

Next, Line 140 determines SA by taking SL from SR("SA=SR−SL"). SA is the ALAY value for the trial. In biofeedback training, this current SA value is to be compared with GL (criterion goal in Line 160 in the "REINFORCEMENT" section) to determine whether or not the reinforcement sound will be given. This is presently a 400 Hz sine wave.

The reinforcement duration (Line 65: variable RW) is chosen to be at least as long as the epoch used. Values of 55 for RW yield about 500 msec for the reward sound. Thus, for 500 msec epochs, the reward tone stays on until the end of the next trial so that if the subject generates a successful SA value on n trials in a row, the reinforcement tone will remain continuously on through n+1 epochs, since experience teaches that brief "pips" for rewards may be disruptive to biofeedback training. However, the program proceeds rapidly to the next trial (Line 178) even while the tone is still on from the current trial, i.e., Line 162, which may turn on the reward tone, is executed instantly (a millisecond or two) while the reward tone endures in "hardware" as the next trial begins to proceed.

Running a baseline with no tones on and then determining values (from such a baseline) on which to calculate a GL value has its disadvantages: Changes in ALAY produced by the mere presence of a new stimulus—the reward tone—are likely to occur in early training even before a subject has learned any voluntary ALAY control. This can retard real learning. Thus, baselines are best collected with a randomly occurring reinforcement tone, the occurrence probability chosen to match that which the subject will receive—contingent on his generating a criterion-reaching ALAY value—when first placed in training. The tone stimulation conditions thus are made consistent from baseline to early training. The baseline ALAY values thus should incorporate the consequences of occurrence (by chance) of the mere stimulation effects of reinforcement signals. Baseline should be different than training only in that the tones are contingent on criterion-reaching ALAY values in training; in baseline, tones occur non-contingently (randomly). This is accomplished by Lines 66, 158, and 159: If the operator specifies (Line 66) baseline, he then gets to specify a baseline random tone rate (determined by Lines 66, 159) and the second part of Line 162 is skipped.

It is noted that the present methodology observes an epoch of $\geq 500$ msec of ALAY after which a reward may be earned depending on the value of ALAY for the entire epoch. This "chunking" method of giving feedback based on a relatively long-enduring "chunk" of EEG has been reported superior in another published paper (Furumitsu et al., *Psychophysiology*, V. 28, 1991, p. S24) to the conventional method of instantly rewarding each criterion-exceeding value (based on <2 wave lengths).

Interposed between in the MATH & RECT and REINFORCEMENT sections is the DISPLAY OPTION (Lines 142–150). This section can display a subset of the RR rectified L(SM) and R(SM) values for the operator to view. The subset can vary from 1 to all RR points. (This is determined by the "DRAWSTEP", Line 85.) The operator does not always need to view the display, and it takes time to display the points. That is, if the epoch of sampling endures 500 msec, the rectification and arithmetic will take about 250 msec more. As noted, the reward Line (162) is executed virtually instantaneously, so that without a display the next trial can begin immediately. With use of a display 36, however, there is a delay before the next trial which will last as long as the display endures. This may be disruptive to training, so it is possible to choose to display only a fraction (e.g., 10%) of the RR points per EEG channel, which will cause a tolerably brief delay, yet provide enough of a display 36 for an operator to monitor and control the quality of the EEG, i.e., to be certain of its freedom from artifact. Alternatively, an auxiliary oscilloscope display 38 of EEG channels can be provided to the operator 33. This is the ongoing, unfiltered EEG from both leads (left and right). The eye channel could also be so monitored, although this is not shown in the Figure.

For portable, inexpensive versions of the biofeedback apparatus, it may be preferable in some situations that the auxiliary display not be used and the single, optional computer display would suffice with a reduced number of displayed points.

Prior to proceeding (in Line 178) to the next trial, the program updates the values of six variables in Lines 170 and 175: ZR, ZL, ZA, QR, QL, and QA. These are the sums over trials of SR, SL, SA, $(SR)^2$, $(SL)^2$, and $(SA)^2$, respectively. (Actually, the sums are the variables divided by "CT" which is set =100 in Line 70. The divisions are done simply to keep the numbers small enough to be tractable.)

Only ZA(ΣSA) and QA(Σ[SA]²) are necessary to obtain in a baseline run in order to do ALAY training later. The other variables are collected for research purposes. From ZA and QA, however, the average and standard deviation of ALAY for the subject can be calculated (as in Lines 182 and 187).

The criterion for reinforcement/reward in operant brain wave training has been defined statistically in much previous research: (Rosenfeld, J. P. and Rudell, A. P. Mediation of operant controlled neural activity. In: D. Mustovsky (Ed.), *Behavior Control and Modification of Physiological Activity*, New York: Appleton-Century-Crofts, 1976; Rosenfeld, J. P. Conditioning changes in the evoked response. In: G. E. Schwartz and J. Beatty (Eds.), *Biofeedback: Theory and Research.* New York: Academic press, 1977, 377–388; Rosenfeld, J. P. and Hetzler, B. E. Significance and mediation of neural and other biofeedback. *International Journal of Neuroscience,* 1979, 8, 233–250; Rosenfeld, J. P., Stamm, J., Roger, M., Birbaumer, N., Rockstroh, B., and Elbertt, T. Biofeedback of event-related potentials. In: Karrer, R., Cohen, J., and Teuting, P. (Eds.), *Brain and Information: Event-Related Potentials,* Proc. VI Int. Conf. on Event-Related Slow Potential of the Brain. N.Y. Acad. Sci., Monograph #12, 1983, 653–666; Rosenfeld, J. P. Applied Psychophysiology and Biofeedback of Event-Related Potentials (Brain Waves): Historical Perspective, Review, Future Directions. *Biofeedback and Self-Regulation,* 15, 1990, 99–120). Brain wave variables (including ALAY samples) are safely assumed to have normal (Gaussian) distributions. Thus a "hit" (criterion-reaching response) can be defined as a value of the variable one standard deviation (sd) or some f(sd), from the pre-training mean. Since such a sample (one sd from the pertaining mean) from a normal distribution is known to have a 16% a priori probability (p=0.16) of occurrence; occasional "hits" must occur even when training begins since the neural operant hit response is deviant but with finite probability and thus within the response repertoire of the subject. Such are the traditional required attributes of any to-be-conditioned operant responses (Skinner, B. F. *Contingencies of Reinforcement.* N.Y.: Appleton-Century-Crofts, 1969). When the hit occasionally occurs (p=0.16) by chance in early training, the subject is signalled with the reinforcement sound that his behavior, state of mind or mental image at that moment was the correct one, and that he should try to repeat the mental or behavioral state that caused the reward. As his hit rate becomes >>0.16, the occurrence of learning is inferred. This method has been used with other neural events (i.e., besides ALAY) many times by the present inventor, in brain wave conditioning research (Rosenfeld, J. P. and Rudell, A. P. Mediation of operant controlled neural activity. In: D. Mustovsky (Ed.), *Behavior Control and Modification of Physiological Activity,* New York: Appleton-Century-Crofts, 1976; Rosenfeld, J. P. Conditioning changes in the evoked response. In: G. E. Schwartz and J. Beatty (Eds.), *Biofeedback: Theory and Research.* New York: Academic Press, 1977, 377–388; Rosenfeld, J. P. and Hetzler, B. E. Significance and mediation of neural and other biofeedback. *International Journal of Neuroscience,* 1979, 8, 233–250; Rosenfeld, J. P., Stamm, J., Roger, M., Birbaumer, N., Rockstroh, B., and Elbert, T. Biofeedback of event-related potentials. In: Karrer, R., Cohen, J., and Teuting, P. (*Eds.), *Brain and Information: Event-Related Potentials,* Proc. VI Int. Conf. on Event-Related Slow Potentials of the Brain. N.Y. Acad. Sci., Monograph #12, 1983, 653–666; Rosenfeld, J. P. Applied Psychophysiology and Biofeedback of Event-Related Potentials (Brain Waves): historical; Perspective, Review, Future Directions. *Biofeedback and Self-Regulation,* 15, 1990, 99–120). The reinforcement criterion can be made increasingly or decreasingly challenging as necessary to facilitate learning.

In baseline sample runs, with the reinforcement signal turned off or given at random, the baseline (pre-training) sampling distributions of ALAY with its properties, (i.e., mean and standard deviation) are determined and output. (See Appendix 2 which is a sample output of the compiled program "(M-)ALAY11" the source code of which is included in Appendix 1 as ALAY11 and which is run on the computer 24 of the Figure to carry out this embodiment of the invention.) Inactivating the reinforcement is done by typing in a value of zero (∅) in Line 65 for "REWARD DUR". Thus, the artifact signal can be used in baseline to train the subject (in baseline) to hold still and refrain from blinks and other movements, while the reward signal is off; (or, of course, random, non-contingent reward signals may be given, as discussed above). Sometimes, the artifact signal is also disruptive to ALAY training; it too can be inactivated by making its duration =zero, while the program nevertheless silently continues to reject artifact-contaminated data by restarting a trial when an artifact is detected).

Since the parameters mean and standard deviation are divided by 100 prior to output, in order to set a reasonable training criterion when the program asks (Line 65) for the "CRITERION TO BEAT," one goes through the following steps: (1) one examines the pretraining average ALAY value for a session, "ZA" in FIG. 2 =0.247. The real value is 24.7(=0.247×100). Suppose one wants to use a "hit" criterion of one standard deviation above the mean. The standard deviation (÷100) is given in the output (Appendix 2) as "SD/A =0.406722674." Multiplying by 100 and rounding the actual value =41. The criterion would then be set at 24.7+41, which is approximately 66; this integer value would be input (to the GL variable) for a subsequent retraining session. It may prove advantageous to take several sessions' worth of samples over, say, a week or month of observations to ascertain the stability of ALAY distribution values of a given subject.

The output (Appendix 2) also gives some time values, which can be used for research or therapy. For example "EPOK" is the duration (epoch) for recording; it is determined by Lines 105 ("B=TI") and 127 ("A=TI"). A and B are reading of the internal computer clock ("TI") before and after the epoch. The units are sixtieths of a second. Thus Line 182 calculates and outputs the epoch as (A−B) ÷60 in seconds. Other program durations in the output are obtained similarly; e.g., "MATH," "DISP," "REINFDUR," "DPOK," (display epoch), etc. The "RES" (resolution) is the number of msec per EEG sample set, and equals EPOK ÷RR. "HITS" is the number of criterion-reaching responses of the set of trials just run. Other recorded information (subject's name, criterion used, etc.) are also output, i.e., echoed form the operator input.

Protocol

The specific protocol used with subjects (in the embodiment) is as follows: After the subject is instrumented with electrodes with <600 ohms difference between left and right electrode impedances, he sits in a comfortable recliner, fills out a depression inventory test (e.g. a Beck Depression Inventory or "BDI") and is told that EEG correlates of emotion are of interest. He is given 2-3 baseline sessions of 10 minutes each (300-600 trials/session) in which both the artifact and reward tones are presented. The artifact tone presentation is indeed based on actual artifact sources and the subject is told from the outset to try to keep still and minimize blinking and eye movements. This instruction will be in force throughout all sessions. The reward tone in baseline, however, is given on a random 15-20% of the trials, as discussed above. The subject is told truly that the reward tones are given randomly in baseline.

Next, the subject has an exploration session of 10 minutes. The reward tones are made contingent on the presence of a certain amount of ALAY, the particular GL value being based on the baseline statistics, as described above. At present, the GL value is set to ZA+0.8(SD/A), these values (ZA, SD/A) coming from the previous baselines runs. This yields about a 15-20% contingent reinforcement rate. The subject is told that the tones now will not now be random and will correlate with his mental state. However, he is not yet told explicitly to alter the ALAY, i.e., to turn the tones on. He is told that he should try to explore what types of mental images and contents turn the tones on.

Finally, he receives 1-2 10 minute training session prior to which he is told to try and maximize reward tone occurrence. He is told that if he can double or better the originally projected hit rate (17%) we will give him $5; if he can triple it, $10; quadruple it or better, $25.

BDI depression inventories are administered again after all sessions.

In a further embodiment, no artifact tones are present at any time. The presence of an artifact is detected and starts a new trial.

In another embodiment, the baseline training is conducted on a separate day. For example, an entire hour on a separate day is devoted to training of four 10-minute sessions. Then, during a separate, subsequent five day period, exploration and training is conducted in four to five 10 minute sessions.

Multiple Leads

It was noted above that in additional embodiments, it may be demonstrated that the ALAY training is more effective if more than one pair of sites is used to obtain brain waves. In other words, since depressed persons have been sometimes reported to show not only more left than right frontal alpha, but also more right than left parietal alpha, it may be that training decreased left frontal (relative to right frontal) and, concomitantly, increased right parietal alpha (relative to left parietal) may be more therapeutically beneficial, than training just the frontal ALAY alone. In that case, the program described in the preceding section would be simply modified as follows: The 1-dimensional array variables L(SM) and R(SM) would be made into 2-dimensional variables L(SM, FP) and R(SM, FP) for frontal left and right leads (FP=1), and now all four channels are sampled (requiring changes in Lines 102-111 of ALAY11), and the 2 new 2-dimensional variable values with FP=2 would be introduced to input L(SM, FP) and R(SM, FP) and all parietal channels. This would, of course, necessitate 2 additional EEG channels, alpha filters, and A/D converters. The variables SR and SL (Line 140) would now be dimensioned as SR(FP) and SL(FP), and very importantly, SA (the ALAY index—see Line 140) would become SA(FP) with FP=1 for frontal SA and FP=2 for parietal SA, respectively. Most importantly, Line 162 would now be "IF SA(1)>GL(1) AND SA(2)<GL(2)THEN I=I+1:SOUND . . . [etc]." That is, both frontal and parietal ALAY variables would need to exceed criteria for reinforcement. The distributions of ALAY collected in baseline sessions would need to be conjoint distributions of frontal and parietal ALAY. (See the method of the present inventor for this approach, Rosenfeld, J. P. Real time processing of event related potentials. In: *Digital Signal Processing*, ed. by R. Weitkunat, Amersterdam: Elsevier, 1991, 279-290).

This method of introducing other ALAY values for multiple pairs of left-right electrodes could be extended to any number of pairs.

Applications

One application of the above described embodiments is in the treatment of depressed persons of all kinds, i.e., in both mildly and more deeply depressed states, of both recent and long term standing, of reactive or endogenous natures, etc. However, the method could also be used as an adjunct in conjunction with other treatments for depression, e.g., psychotherapy and/or pharmacotherapy. The method could also be used prophylactically, in that Henriques and Davidson (*J. Abnormal Psych.*, Vol. 99, 22-31, 1990) have reported ALAY anomalies in persons who had been depressed but were not depressed at the time of testing. Eventually, all persons with family histories of depression (or, indeed, all persons) could be screened for ALAY anomalies, and the corrective ALAY re-training would proceed with home practice units.

Even more generally, since left-right EEG asymmetry has been associated with various emotional states (Robinson et al. (1984), *Brain*, 107, 87-93), manipulating an existing left-right pattern (with ALAY biofeedback) in any given person could be expected to manipulate a corresponding variety of affective states, in addition to depression: For example, the manic state has been associated with right hemisphere inactivation (Robinson et al. (1984), *Brain*, 107, 87-93) (complimenting the association of depression with left inactivation). An appropriate ALAY conditioning paradigm could thus be developed to treat mania before (prophylaxis) or after symptoms development.

It may also be possible to increase diagnostic sensitivity with depressives by classifying them on the degree to which their ALAY may be modified with bio-feedback. Thus ALAY-bio-feedback modifiability would constitute an index, providing an additional application of the invention in psychodiagnosis.

Other Embodiments

There are a variety of parametric choices of variable values which have been noted here for these embodiments of ALAY conditioning. Just as the number of sites may change, the following presently utilized program parameters and hardware attributes may change, without altering the essential conceptual basis of the invention.

Regarding hardware, (1) 8-bit A/D converters with 2 $\mu$sec conversion times are presently used. Any $\geq 8$ bit value A/D units are acceptable, providing conversion times remain low enough to maintain $\geq 200$ Hz sampling rates for all sites. (2) Any microcomputer may be used. (3) The intertrial (inter-epoch/sample) interval is now zero. A slight delay may prove beneficial. (4) Indeed, the temporal relationships of epoch-duration and inter-trial interval may require conjoint adjustment for optimal training. It may be useful to introduce rest periods. (5) The rewards criterion and shaping method may be adjusted. Presently, a criterion (GL value)=ZA +0.8(SD/A) is used, which has about a p=0.20 a priori (pre-training) chance occurrence rate. As the subject begins to learn, a shaping procedure (using ZA +0.9(SD/A)) may prove to speed learning.

Biofeedback Using Asymmetries of Other Brain Wave Frequencies

Although the various embodiments preferably use biofeedback control of alpha brain wave (8–12 Hz) asymmetry, other types of brain waves may be used, either alone or in combination with other waves including alpha waves, to obtain similar results. Further, use of various types of brain waves, alone or in combination with each other, may have advantages for treatment of certain conditions or for effecting certain desired results.

For example, asymmetry of other EEG frequencies, such as Beta (13–30 Hz) and theta (4–7 Hz), as well as other frequencies, may be related to psychopathology. Regarding Beta activity, it is noted that alpha and Beta are usually reciprocally present anyway. Alpha and Beta are reciprocal indicators of cortical activation so that asymmetries of these frequencies index differential right-left-cortical general activation. When a piece of cortex is relaxed or idling, it generates synchronous, high amplitude alpha, whose power is up while Beta power could be down. When the piece of cortex is aroused, alerted, or busy, the alpha is substantially absent (low power) and an asynchronous low amplitude Beta emerges (increased Beta power). Thus, Beta brain wave asymmetry could be used rather than alpha brain wave asymmetry, although the direction of biofeedback training to reduce the undesired pathological condition would be reversed. For alpha asymmetry training for depression therapy, one increases the right-minus-left power; whereas for Beta training to achieve the same end, one would train decreases in right-minus-left power.

A further embodiment would combine biofeedback training of increases in right-minus-left alpha power and (i.e., along with) decreases in right-minus-left Beta power.

It is noted that since Beta waves are a higher frequency, they are more susceptible to higher frequency muscular artifact interference. Using Beta may require additionally recording and subtracting harmonics of electromyographic (EMG-muscle) activity which may leak into the Beta channel.

Regarding the use of theta brain waves (4–7 Hz), and other frequencies, it may be possible to use these waves as well. It has been reported that theta brain wave activity at a site correlates with emotional release, and transitions of mental/emotional status, and imaging. Altering biofeedback asymmetries of theta waves could be used to effect modifications of conditions associated therewith.

Biofeedback Using Brain Wave Asymmetries for Modification of Other Pathologies or Conditions Further embodiments of the invention may be directed to any other disturbances in cognitive and/or emotional functions that one can associate with various alternative EEG asymmetries. It may be desired and possible to attempt to restore normal or desired function by biofeedback modification of the asymmetry in any case of any type of asymmetry-related psychopathology.

Studies have reported associating various psychological disturbances and EEG asymmetry. (Many studies are summarized in John L. Andreassi's text, "Psychophysiology," 2nd ed., Hillsdale, N. J.: L. Erlbaum & Assoc,.publishers, 1989.) For example, it has been long known that the right hemisphere of the brain is involved with holistic and imaging functions, whereas the left hemisphere of the brain is associated with verbal and quantitative skills. Thus, Robbins and McAdam (1974) show greater left activity (more beta, less alpha power) with letter writing and more right activity with image formation. Writing and imaging at the same time produce equal hemispheric activation patterns. Musical and spatial tasks also produce greater right activation. Rugg and Dickens (1982) found a functionally related asymmetry of Theta activity: greater in the right hemisphere during visuospatial versus verbal tasks. Accordingly, in a further embodiment of the present invention, changes in cognitive functioning may be obtained also from EEG asymmetry biofeedback.

It has also been observed that stuttering and other speech disorders are related to left right differences. Accordingly, in a still further embodiment of the present invention, changes in speech disorders may be obtained from EEG asymmetry biofeedback.

Based on the studies of single site EEG frequency correlates of behavior, it may be possible to achieve functional consequences of asymmetry biofeedback of these frequencies. Listed below are some of the other know EEG frequencies and their putative functional significances:

a. Delta (0.5–3.5 Hz). This type of wave is seen only in dreamless sleep in normal individuals. In wakefulness, an excess of it would indicate abnormality, e.g. a tumor or other lesion.

b. Theta (4–7 Hz). This type of wave has been reported to accompany pleasure and displeasure (not neutral feelings). It is more typical of the EEG of babies and children than that of adults. Thus some current investigators use biofeedback to train patients to produce it (at one site, of course), and claim its production results in the release of childhood memories with attendant emotional discharge and augmented therapeutic gains. From this, one can estimate that augmented right versus left theta training might result in release of holistic, non-verbal memories; more left than right would maybe have the opposite effect. Theta has also been long associated inversely with vigilance and attention. Training theta suppression leads to heightened attention (Beatty et al., 1974).

c. Kappa (10 Hz). This type of wave has been associated with thinking. (one paper).

d. Mu (9–11 Hz). This type of wave has been associated with scanning patterned stimuli. Mu has also been associated with inhibition of motor processes.

e. SMR (12–14 Hz). (Sensori-motor rhythm). Sterman et al. have frequently shown this wave to be associated with vulnerability to seizures, i.e. biofeedback of SMR increases leads to reduced seizure occurrence. SMR has also been associated with inhibition of motor processes.

f. Gamma (38–42 Hz) activity. This type of wave was recently studied by serious researchers as associated with cognitive activity, particularly when several sites become active in the 40 Hz band at once.

Based on the above, it may be possible to effect modification of any condition associated with the brain wave activity by identifying an asymmetry activity associated with the condition and using biofeedback to alter the asymmetry. The condition may be a pathological or undesirable condition. However, in a broader sense, use of biofeedback to alter brain wave asymmetry may be used to modify any type of condition or state that is associated with the asymmetry. For example, the above identification of certain conditions or states related to particular brain wave activities may lead to modification of these conditions or states by asymmetry biofeedback training. Asymmetry training may, for example, be used to heighten mental awareness, or musical or artistic appreciation. Such training may even be used to affect temporary changes in a person's condition or state.

Biofeedback Use with ERP Asymmetries

The above embodiments may be used with spontaneous ongoing EEG. People have also studied asymmetries in amplitudes of evoked EEG responses, e.g., event related potentials (ERPs) such as P300. That is, functional correlates of ERP asymmetries have been studied. As may be expected from the material presented above, ERP amplitudes are bigger over left hemispheres than right in response to verbal stimuli. More interesting is the often reported finding that ERPs are larger over the right than the left hemisphere in bright children, but not in dull children. Normal children also have bigger ERPs in right hemisphere relative to left, than do retarded children. Thus, biofeedback control of ERP asymmetry could be used to improve cognitive function.

It has been shown that biofeedback control of ERP can be readily done in cats, rats, and people, and there are major functional consequences, e.g., Rosenfeld and colleagues have shown numerous times that biofeedback modification of ERPs in the cortex associated with pain perception leads to correlated changes in pain tolerance (Rosenfeld et al., 1984). However, brain wave frequency is usually not analyzed when considering ERPs although one could. Typically, only the amplitude or latency of a particular ERP component are observed, e.g. P300. In spontaneous EEG, one usually looks at power spectra, i.e. frequency data. The implication here is that different brain wave measurements are used and one reinforces or rewards amplitude and latency differences rather than power differences. Methods of biofeedback for single site ERP modification have been reported. These methods may be extended to combinations of sites as in asymmetry biofeedback.

Elimination of EMG Artifacts

If higher frequency EEG is used (i.e. anything higher than alpha) there is a possibility of interference from muscular artifacts. EEG is recorded from scalp. There are muscles in the scalp that generate electromyographic activity (EMG). This activity is mostly in the 100–5000 Hz range (above the EEG range which is mostly from 0–50 Hz), but there is some EMG activity in the 10–50 Hz range. This could erroneously be taken as EEG activity. Therefore in training production of any EEG activity, one needs to know when EMG is present in the scalp leads, and one needs to give a subject feedback to this effect so as to get him/her to desist generating it. The usual way to do this is to take the signal from each scalp lead and pass it into two channels, a high channel which looks at pure EMG (100–5000 Hz) and a low channel for EEG and maybe some EMG contamination. Whenever the high channel shows some EMG, turn off all reward signals and sound a special signal (or shine a special light) to tell the subject to desist, relax, etc. Only when the EMG high channel is silent does one look at other channels for pure EEG to submit for biofeedback evaluation.

Alternative Electrode Referencing

In the co-pending application, EEG recorded from a right scalp site, Rn, is referenced to the vertex, Cz, and so is the corresponding left site, Ln. That is, these are BIPOLAR recordings. In Alpha asymmetry and other neurofeedback approaches, this may be preferable since midline bipolar recordings are relatively free of EMG artifact, and the problem of PHASE EFFECT CONFOUNDING has been avoidable. This effect refers to the obtaining of spurious power difference values which are more related to Rn/Ln phase differences, in which this invention is not primarily interested, rather than actual frequency power differences (Rn-Ln) which is the subject matter of the present invention. This confounding may be avoided by utilizing standard reference sites for REFERENTIAL or MONOPOLAR recording, instead of Cz. Examples of such sites: Linked ear lobes, Mastoids, LaPlacians, average of all electrodes, etc.

Alternative Biofeedback Techniques

In a usual biofeedback procedure, reward tones are low, and "miss" signals are high. So there is always a tone present and the idea is to keep it low. A possible disadvantage of this technique is that the subject knows only if he has hit or missed, but not how close he came or how well or poorly he did. It would be preferable to provide continuous rather than dichotomous feedback for this. In an alternative embodiment, the biofeedback signal uses a tone whose pitch is proportional to the degree of right-left power difference of whatever frequency is being trained. Assuming the subject has no absolute pitch, the subject knows if he hit or missed because two speakers are provided. Signals from the left speaker indicate a miss, signals from the right indicate a hit. Now the subject is informed whether he has hit or miss and how close he was. Alternatively, one can also use a visual display where a pointer on a scale moves from left to right. A mark in the middle indicates the hit-miss threshold. The kinds of feedback one uses (visual v. acoustic vs. both) depend on what EEG frequency is being trained. It may also help to have pleasant background music, which the subject selects. This music should not be louder than the feedback signals.

It is intended that the foregoing detailed description be regarded as illustrative rather than limiting and that it is understood that the following claims including all equivalents are intended to define the scope of the invention.

Appendix 1

```
5 REM@I = T,01,TR,SM,RR,L(SM),R(SM),AF,ZE,FF,MM,IS,OT,SR,SL,DR,YR(SM),YR(SL),CT,
MS,TC,TP,
6 PRINTCHR$(147) :REX/ALAY111A.RESERVED INTEGERS, BUT COMPILED ON "OPTION 1"
7 PRINT"ALAY11,3-2-91; REV, 5- 2-92,BY J.P. ROSENFELD,PHD. PROGRAM WILL TRAIN OR
    SAMPLE EEG ALPHA OR OTHER 2-SITE ASYMMETRY WITH CORRECT HARDWARE BANDPASS FILT
ER"
8 FOR I=1TO10000:NEXT
10 REM/ ALAY11 (VS 09) HAS RAMREINF OPTION,MORE DEBUGS THAN ALAY10
12 FAST:CLR:DIM R(300):DIM L(300):DIMYR(300):DIMYL(300)
15 PRINTCHR$(147)
21 REM
22 REM.............SET-UP.....................
23 REM
30 O2=2:V1=2500:V2=250:V3=5000:HF=.5:V4=3000 :V6=2048:V6=60:KM=1000
40 VOL 15
65 INPUT"CRITERION TO BEAT";GL:INPUT"DISPLAY(1 OR 0)",DR:INPUT "HARD COPY(0 OR 1)
"HC:INPUT"REWARD DUR";RW:INPUT"AFT SIG DUR";AD:INPUT"S-NAME":NM$
66 INPUT"TRAIN OR SAMPLE(SAMPLE=1,TRAIN=2)";BT :IF BT=1THEN INPUT"RAND. HIT RATE
(1-100)";CC
70 INPUT"DELAY/ITI":IT:INPUT"DELAY/ISMPLI";IS:I=0:WS=160:TE=28:CO=DEC("DF00"):C1
=DEC("DF01"):C2=DEC("DF03"):01=1:ZE=0:OT=128:FF=255:CT=100:K1=50/128 :TC=300
80 SCNCLR
85 INPUT"DRAWSTEP (USUALLY =1 SO DRAWPOK=EPOCH)";DP:COLOR 0,1:COLOR 1,2:COLOR 4,
1:GRAPHIC 1,1
90 INPUT"SWEEPS/TRIALS(2500)";TR
95 INPUT"EPOCH PTS(*RES=EPOK . . . 300MAX)";RR:TP=INT(300/RR)*DP:INPUT"HI";HI:INPUT"
LO":LO
96 REM
97 REM...............TRIALS LOOP............
100 FOR T=01TOTR:GRAPHIC 1,1:SL=ZE:SR=ZE
101 REM
102 REM..........EEG SAMPLING LOOP....
103 REM
104 DD=PEEK(C0):DD=PEEK(C1) :REM/ DUMMY 2-STEP SETUP
105 B=TI:FOR SM=01TORR :REM/=.5 SEC AT 5 MSEC RES IFRR=100
110 L(SM)=PEEK(C2):REM RETURNS C0
111 R(SM)=PEEK(C0):REM RETURNS C1
112 AF=PEEK(C1):IF AFK<=LO OR AF>=HI THERSOUND 02,V1,AD,02,V2,V3,01,0:IA=IA+1:ELS
EGOTO127:REM RETURNS C2 WHICH IS EYE CHANNEL
126 GOTO 105
127 FORMM=01TOIS:NEXTMM:NEXT SM:A=TI
128 REM
129 REM............RECT & MATH..........
130 B1=TI: FORSM=01TORR:IF R(SM)<OT THEN R(SM)=FF -R(SM):ELSE R(SM)=2E+R(SM)
135 IF L(SM)<OT THEN L(SM)=FF -L(SM):ELSE L(SM)=ZE+L(SM)
140 SR=SR+R(SM):SL=SL+L(SM):NEXTSM:SA=SR-SL:A1=TI
141 REM
142 REM..........DISPLAY OPTION.......
145 IF DR=ZE THEN GOTO 158:REM/ SKIP DRAW OPTION
148 D=TI:FOR SM =01 TO RR:YR(SM)=R(SM)*K1:YL(SM)=L(SM)*K1,CT:NEXT SM
150 SM=1: SLOW:FORMS=01TOCSTEPTP: DRAW 01,MS,YR(SM):DRAW 01,XS,YL(SM):SM=SM+01
    NEXTMS:C=TI:FAST :FORLL=01TOIT:NEXTLL
151 REM
152 REM..........REINFORCEMENT........
158 RD=TI:ON BT GOTO 159,162
159 NR=INT(RND(1)* CT+01):IF NR< CC THEN IR=IR+1:SOUND 01,V4,RW,ZE,ZE,ZE,ZE,V5
162 IFSA >GL THENI=I+01:IFBT=2 THEN SOUND 01,V4,RW,ZE,ZE,ZE LE,V5
163 RC=TI
164 REM
165 REM..........STATS. END LOOP......
170 ZR=ZR+SR/CT :ZL=ZL+SL/CT :ZA=ZA+SA/CT
175 QR=QR+(SR/CT) ↑ 02,QL=QL+(SL/CT) ↑ 02:QA=QA+(SA/CT) ↑ 02
178 NEXT T
180 REM
181 REM............RUN STATS/SCREEN OUTPUT.........
182 PRINT"ZR=" ZR/TR:"ZL=" ZL/TR;"ZA="ZA/TR:"HITS=" I:
"EPOK="(A−B)/60:"MATH="(A1−B1)/V6;"DISP="(C−D)/V6:"REINF="(RC−RD)/V6
185 VL= ((TR*QL−ZL ↑ 02)/(TR*(TR−01))) ↑ HF
186 VR= ((TR*QR−ZR ↑ 02)/(TR*(TR−01))) ↑ HF
187 VA= ((TR*QA−ZA ↑ 02)/(TR*(TR−01))) ↑ HF
188 PRINT"SD/L="VL;"SD/R="VR:"SD/A="VA
189 REM
190 REM...........OUTPUT/HARD COPY OPTION........
191 REM
192 IFHC>OTHENOPEN4,4:CMD4:PRINT"ZR=" ZR/TR,"ZL=" ZL/TR,"ZA="ZA/TR,
"HITS=" 1,"EPOK="(A−B)/V6,"MATH="(A1−B1)/V6,"DISP="(C−D)/V6;
"REINF="(RC−RD)/V6:ELSE GOTO200
193 PRINT"AFTS="IA,"RANHITS="IR,"HI="HI,"LO="LO
195 PRINT"SD/L="VL,"SD/R="VR,"SD/A="VA,"CRIT="GL,"ISMFLI="IS,"ITI=IT
196 PRINT"REINFDUR="RW,"AFT SIG DUR="AD,"S-NAME="NM$
197 PRINT"DPOK="300/TP*(((A−B)/V6)/RR)*KM,"TP="TP,"QR="QR/TR,
```

-continued

Appendix 1

"QL="QL/TR,"QA=QA/TR
199 PRINT"TRIALS="TR,"RES="(((A−B)/V6)/RR)*KM:PRINT#4:CLOSE4
200 INPUT"RUN AGAIN(1/0)";AG:IFAG>OTHEN RUN 12:ELSE END

Appendix 2
Output of (M-)ALAY11
NOTE: When compiled, ALAY11 is called M-ALAY11

| R= 139.495 | ZL= 139.248 | ZA= .247 | HITS= 8 |
|---|---|---|---|
| EPOK= .383333333 .0166666667 | MATH= .183333333 | DISP= .283333333 REINF | |
| D/L= .630674752 | SD/R= .643622208 | SD/A= .406722674 | |
| CRIT= −9 | ISMRLI= 10 | ITI= 0 | |
| EINFDUR= 55 | AFT SIG DUR= 55 | S-NAME=R | |
| POK= 59.8958333 35 | TP= 24 | QR= 19459.2279 | QL= 19390.3 |
| | QA= .20989 | | |
| RIALS= 10 | RES= 4.79166667 | | |

I claim:

1. A method for modifying a condition of a patient, said condition being characterized by asymmetry between brain waves measured from at least two different locations of the patient's scalp, comprising the steps of:
testing the patient for the condition characterized by asymmetry between brain waves from at least two scalp locations;
attaching a first electrode to a first scalp location of the patient;
attaching a second electrode to a second scalp location of the patient;
recording brain waves of the patient from the electrodes; and
rewarding the patient for changing asymmetry between the brain waves recorded from the two scalp locations.

2. The invention of claim 1 wherein the step of recording brain waves further comprises:
recording brain waves other than alpha brain waves.

3. The invention of claim 1 wherein the step of recording brain waves further comprises:
recording brain waves including alpha brain waves and other than alpha brain waves.

4. The invention of claim 1 wherein the step of recording brain waves further comprises:
recording brain waves of more than one type.

5. The invention of claim 1 wherein the step of recording brain waves further comprises:
recording asymmetries of event related potentials.

6. The invention of claim 1 wherein the step of rewarding the patient for changing asymmetry further comprises:
rewarding the patient for changing asymmetry of more than one type of brain wave.

7. The invention of claim 1 wherein the step of recording brain waves records brain waves of one type and wherein the step of rewarding the patient for changing asymmetry utilizes brain waves of the same type.

8. The invention of claim 1 wherein the step of rewarding the patient for changing asymmetry further comprises:
rewarding the patient for changing asymmetry of beta waves.

9. The invention of claim 1 wherein the step of rewarding the patient for changing asymmetry further comprises:
rewarding the patient for changing asymmetry of beta waves and alpha waves.

10. The invention of claim 1 wherein the step of rewarding the patient for changing asymmetry further comprises:
rewarding the patient for simultaneously changing asymmetry of beta waves and alpha waves.

11. The invention of claim 1 wherein the step of rewarding the patient for changing asymmetry further comprises:
rewarding the patient for changing asymmetry of beta waves and alpha waves in opposite directions.

12. The invention of claim 1 wherein the brain wave is of a type selected from a group consisting of:
a. alpha waves,
b. beta waves,
c. theta waves,
d. kappa waves,
e. mu waves,
f. SMR waves,
g. 10 Hz waves,
h. 9–11 Hz waves,
i. 12–14 Hz waves,
j. Gamma waves.

13. The invention of claim 1 wherein the brain waves have a frequency selected from a group consisting of:
0.5–3.5 Hz, 4–7 Hz, 6–7 Hz, 8–12 Hz, 9–11 Hz, 10 Hz, 12–14 Hz, 13–30 Hz, and 38–42 Hz.

14. The invention of claim 1 wherein the step of rewarding the patient for changing asymmetry between the brain waves further comprises:
rewarding the patient for changing asymmetries of brain wave event related potentials.

15. The invention of claim 1 further comprising the step of:
reducing artifacts of electromyographic and other artifactual activity.

16. The invention of claim 1 in which the method further comprises the step of:
providing the patient with biofeedback for reducing electromyographic activity.

17. The invention of claim 1 in which the method further comprises the steps of:
recording electromyographic activity,
presenting the patient with information indicative of the electromyographic activity; and
withholding rewarding the patient until electromyographic activity is reduced.

18. The invention of claim 17 in which the step of rewarding the patient for changing asymmetry between the brain waves recorded from the two scalp locations is performed only after the step of rewarding the patient for reducing the electromyographic activity.

19. The invention of claim 1 further comprising:

presenting the patient with information of a relative degree of brain wave asymmetry.

20. The invention of claim 1 further comprising:

presenting the patient with information of a relative degree of brain wave asymmetry, and additionally presenting the patient with information indicative that the brain wave asymmetry has been reversed relative to the asymmetry characteristic of the unmodified condition.

21. The invention of claim 1 wherein the condition being modified comprises at least one of: depression, stuttering, retardation, cognitive ability, seizures emotional disorders, performance disorders, and attention disorders.

* * * * *